(12) United States Patent
Buddharaju

(10) Patent No.: US 11,337,848 B1
(45) Date of Patent: May 24, 2022

(54) MALE EXTERNAL CATHETER

(71) Applicant: Venkata Buddharaju, Park Ridge, IL (US)

(72) Inventor: Venkata Buddharaju, Park Ridge, IL (US)

(*) Notice: Subject to any disclaimer, the term of this patent is extended or adjusted under 35 U.S.C. 154(b) by 0 days.

(21) Appl. No.: 17/132,842

(22) Filed: Dec. 23, 2020

(51) Int. Cl.
| | |
|---|---|
| *A61M 5/32* | (2006.01) |
| *A61F 5/44* | (2006.01) |
| *A61F 5/453* | (2006.01) |
| *A61M 1/00* | (2006.01) |
| *A61M 27/00* | (2006.01) |

(52) U.S. Cl.
CPC ............ *A61F 5/453* (2013.01); *A61F 5/4408* (2013.01)

(58) Field of Classification Search
CPC .......... A61M 5/32; A61M 1/00; A61M 27/00; A61F 5/44; A61F 5/453; A61F 5/4408; A61B 19/00
See application file for complete search history.

(56) References Cited

U.S. PATENT DOCUMENTS

| | | | | |
|---|---|---|---|---|
| 4,994,051 A | * | 2/1991 | Walsh | ..................... A61F 5/453 604/349 |
| 2012/0029452 A1 | * | 2/2012 | Rodsten | ................ A61F 5/4408 604/353 |

* cited by examiner

*Primary Examiner* — Tatyana Zalukaeva
*Assistant Examiner* — Ilya Y Treyger
(74) *Attorney, Agent, or Firm* — K&L Gates LLP

(57) ABSTRACT

A male external catheter includes a base and a body. The base includes a planar body and an opening, wherein the planar body includes a first planar surface and a second planar surface opposite the first planar surface. The body extends from the second planar surface of the base and has a tubular shape about the opening of the base. The body also includes a base portion adjacent to the base and having a base wall thickness; a tip portion distal from the base and including a tip configured to connect to the tubing of the drainage bag, wherein the tip portion has a tip wall thickness; and a central portion between the base portion and the tip portion and having a central wall thickness. The central wall thickness is less than at least one of the base wall thickness and the tip wall thickness.

20 Claims, 4 Drawing Sheets

MALE EXTERNAL CATHETER

BACKGROUND

The present disclosure relates to male external catheters. More specifically, the present disclosure is directed to a male external catheter having varying wall thicknesses that result in a secure fit during use.

Condom catheters are alternatives to indwelling catheters that are less invasive to the patient. A conventional condom catheter is a sheath worn about the penis attached to tubing that directs urine to a drainage bag. The sheath is typically made of silicone and/or latex and includes a uniform wall thickness throughout the height.

An adhesive is typically provided on the interior of the opening of the sheath to adhere the condom catheter to the user's penis. In some catheters, a loop and pile (Velcro™) tape releaseable fastener or other fastener may be used to secure the catheter about the penis.

Users of conventional condom catheters often experience pain or discomfort during use. The latex material may irritate the user's skin, and users often cannot anticipate having a reaction until the catheter is applied to the penis. Further, adhesives and other elements used to secure the catheter in place on the penis often get caught on the user's sensitive skin and hair within the region, leading to more acute pain. The adhesive material often times attaches too hard and tight around the penile skin, causing swelling, skin damage, and discomfort during use and/or removal. When left in place for too long, localized skin removal and/or wound formation may result, causing the patient to require the insertion of an indwelling catheter into the urethra and bladder for urinary drainage. Indwelling catheters increase the risk for urinary tract infections.

Another significant problem faced by condom catheters is leakage as well as difficulty retaining the condom catheter in place. Prior art systems including mechanisms to secure the condom catheter in place, such as complex belts with straps and/or adhesives. Belt systems tend to be cumbersome and uncomfortable, and do not ensure that leakage is avoided. Similarly adhesives may include gaps formed during application through which urine escapes. When urine and sweat interact with the adhesives, which is especially common in the pubic area having hair, the adhesive can become dislodged, resulting in leakage and needing to be replaced frequently, causing further pain and discomfort as well as increased health care costs.

Accordingly, there is a need for a male external catheter that minimizes leakage without utilizing adhesives or other additional components, as described herein.

SUMMARY

To meet the needs noted above and others, the present disclosure provides a male external catheter that conforms or adapts to the size and fit around the user's penis as urine flows through, thereby maintaining its positioning without the need for adhesives or other securing mechanisms while reducing the likelihood of leakage. The male penis varies in size during flaccid and semi-flaccid states throughout the day and night. The presently claimed male external catheter stretches and adapts to the male penis size throughout the changes, conforming to the size and remaining soft on the skin so as to improve patient comfort. The male external catheter described herein is reusable, reducing waste as well as healthcare costs.

The body of the male external catheter has a tubular shape with a varying cross-sectional area along a height thereof. The body includes a base portion, a central portion, and a tip portion, with the base portion being adjacent to the base and the tip portion configured to connect to tubing of a drainage bag. Each of the base portion, the central portion, and the tip portion include a base wall thickness, a central wall thickness, and a tip wall thickness, respectively. The central wall thickness is less than each of the base wall thickness and the tip wall thickness. This difference in wall thicknesses enables the central portion of the sheath to collapse around the user's penis while urine flows through the sheath and tip into the drainage bag.

In one embodiment, the base is a planar body providing a frame for an opening through which the penis extends during use. The planar body includes first and second side portions that include first and second strap openings, respectively. An elastic strap may be fixedly or removably attached to the base at the strap openings and extend around the waist of the user during use.

The base portion of the body may be formed integrally with the base. The base portion has a base height $h_b$ of approximately 0.830 in, although the base height $h_b$ may vary as desired or required during manufacturing. The base wall thickness $t_b$ is preferably about 0.060 in at the greatest point, although the base wall thickness $t_b$ may vary as desired or as required during manufacturing. In some embodiments, the base wall thickness $t_b$ tapers from a predominant base wall thickness $t_{b-p}$ to the central wall thickness $t_c$ near the juncture of the base portion 102a and the central portion 102b. In one embodiment, the predominant base wall thickness $t_{b-p}$ is about 0.060 in. In one embodiment, the base wall thickness tapers from a predominant base wall thickness to the central wall thickness near the juncture of the base portion and the central portion.

The central portion of the body includes a planar section adjacent to the base portion and a bellowed section adjacent to the tip portion. The bellowed section may include one or more horizontal bellows transverse to the height H of the body. In some embodiments, the planar section may include optional vertical ribbing leading up to and connected to the horizontal bellows. The vertical ribs may be evenly positioned along the perimeter of the body at or near the juncture of the planar section and the bellowed section. The central portion has a central height $h_c$ of about 1.514 in, although the central height $h_c$ may vary as desired or required during manufacturing. The central wall thickness $t_c$ is preferably about 0.030 in, although the central wall thickness $t_c$ may vary as desired or as required during manufacturing.

The tip portion of the body has a tip height $h_t$ of about 1.315 in, although the tip height $h_t$ may vary as desired or required during manufacturing. The tip wall thickness $t_t$ is preferably about 0.060 in although the tip wall thickness $t_t$ may vary as desired or required during manufacturing. In some embodiments, the tip portion includes horizontal ribbing along the perimeter of the cylindrical body.

During use, the user expands the opening in the base and inserts the penis through the base and into the body. As urine flows through the tip portion, the central portion of the body is pulled toward the penis and holds the user's penis.

In light of the disclosure set forth herein, and without limiting the disclosure in any way, in a first aspect, which may be combined with any other aspect or portion thereof described herein, a male external catheter that connects to tubing of a drainage bag includes a base having a planar body and including an opening, wherein the planar body includes a first planar surface and a second planar surface opposite the first planar surface; and a body extending from the second planar surface and having a tubular shape about the opening of the base, the body including: a base portion adjacent to the base and having a base wall thickness; a tip portion distal from the base and including a tip configured to connect to the tubing of the drainage bag, wherein the tip portion has a tip wall thickness; and a central portion between the base portion and the tip portion and having a central wall thickness; wherein the central wall thickness is less than at least one of the base wall thickness and the tip wall thickness.

In a second aspect, which may be combined with any other aspect or portion thereof described herein unless otherwise specified, a ratio of the central wall thickness to one of the base wall thickness and the tip wall thickness is at least 1:1.25.

In a third aspect, which may be combined with any other aspect or portion thereof described herein unless otherwise specified, a ratio of the central wall thickness to one of the base wall thickness and the tip wall thickness is at least 1:1.5.

In a fourth aspect, which may be combined with any other aspect or portion thereof described herein unless otherwise specified, a ratio of the central wall thickness to one of the base wall thickness and the tip wall thickness is at least 1:2.

In a fifth aspect, which may be combined with any other aspect or portion thereof described herein unless otherwise specified, the central portion includes a planar section adjacent to the base portion and a bellowed section adjacent to the tip portion.

In a sixth aspect, which may be combined with any other aspect or portion thereof described herein unless otherwise specified, the body has a height extending from the first planar surface of the base to a tip end surface on the tip, wherein the bellowed section includes horizontal bellows transverse to the height of the body.

In a seventh aspect, which may be combined with any other aspect or portion thereof described herein unless otherwise specified, the base portion has a base height of approximately 0.830 in.

In an eighth aspect, which may be combined with any other aspect or portion thereof described herein unless otherwise specified, the base wall thickness varies along the base height and includes a predominant base wall thickness, and wherein the central wall thickness is less than the predominant base wall thickness.

In a ninth aspect, which may be combined with any other aspect or portion thereof described herein unless otherwise specified, the base wall thickness tapers to the central wall thickness where the base portion of the body meets the central portion of the body.

In a tenth aspect, which may be combined with any other aspect or portion thereof described herein unless otherwise specified, the base and the body comprise a silicone material.

In an eleventh aspect, which may be combined with any other aspect or portion thereof described herein unless otherwise specified, the base and body are free from latex.

In a twelfth aspect, which may be combined with any other aspect or portion thereof described herein unless otherwise specified, the base and body are free from adhesive.

In a thirteenth aspect, which may be combined with any other aspect or portion thereof described herein unless otherwise specified, a male external catheter that connects to tubing of a drainage bag includes a base having a planar body with a first planar surface and a second planar surface opposite the first planar surface, wherein the base includes a central opening and first and second strap openings on opposite sides of the central opening; and a body extending from the second planar surface and having a tubular shape about the opening of the base, the body including: a base portion adjacent to the base; a tip portion distal from the base and including a tip configured to connect to the tubing of the drainage bag; and a central portion between the base portion and the tip portion.

In a fourteenth aspect, which may be combined with any other aspect or portion thereof described herein unless otherwise specified, the first planar surface of the base has a concave shape.

In a fifteenth aspect, which may be combined with any other aspect or portion thereof described herein unless otherwise specified, each of the first and second strap openings has a slot shape.

In a sixteenth aspect, which may be combined with any other aspect or portion thereof described herein unless otherwise specified, a method of using a male external catheter by a user includes the steps of: providing the male external catheter comprising a base having a planar body and including an opening, wherein the planar body includes a first planar surface and a second planar surface opposite the first planar surface; and a body extending from the second planar surface and having a tubular shape about the opening of the base, the body including: a base portion adjacent to the base and having a base wall thickness; a tip portion distal from the base and including a tip configured to connect to the tubing of the drainage bag, wherein the tip portion has a tip wall thickness; and a central portion between the base portion and the tip portion and having a central wall thickness; wherein the central wall thickness is less than one of the base wall thickness and the tip wall thickness; expanding the opening of the base; inserting a penis of the user through the opening and into the body; and releasing the opening of the base so that the male external catheter remains in position on the penis without the use of an adhesive.

In a seventeenth aspect, which may be combined with any other aspect or portion thereof described herein unless otherwise specified, the method further comprises the step of causing the central portion of the body of the male external catheter to collapse around the penis by releasing urine into and through the tip portion of the body of the male external catheter.

In an eighteenth aspect, any of the features, functionality and alternatives described in connection with any one or more of FIGS. 1 to 6B may be combined with any of the features, functionality and alternatives described in connection with any other of FIGS. 1 to 6B.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION

Figure 1:
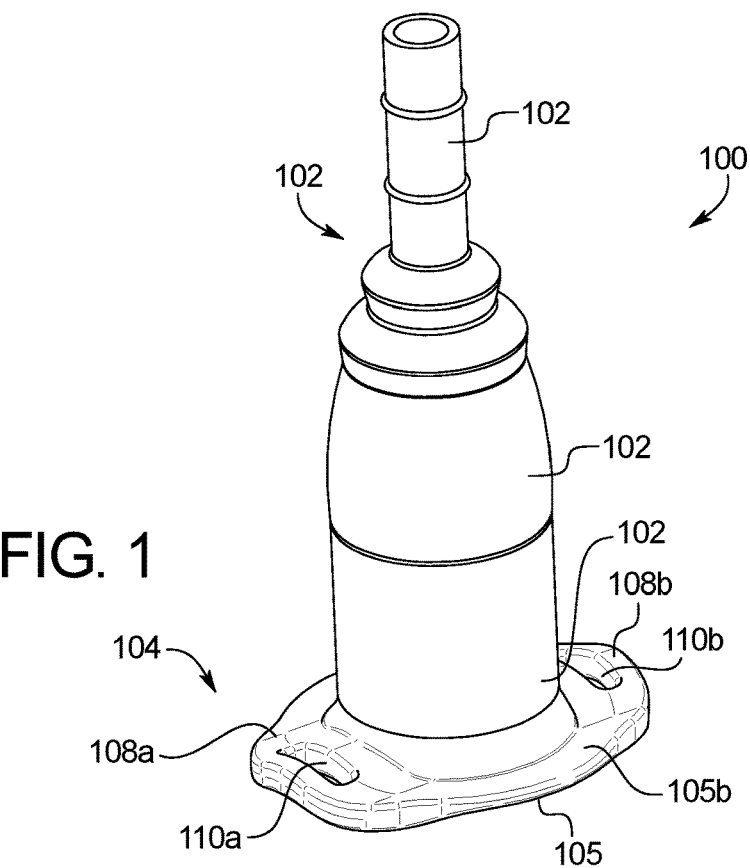
FIG. 1 is a perspective view from above of the male external catheter of the present application.
Figure 2:
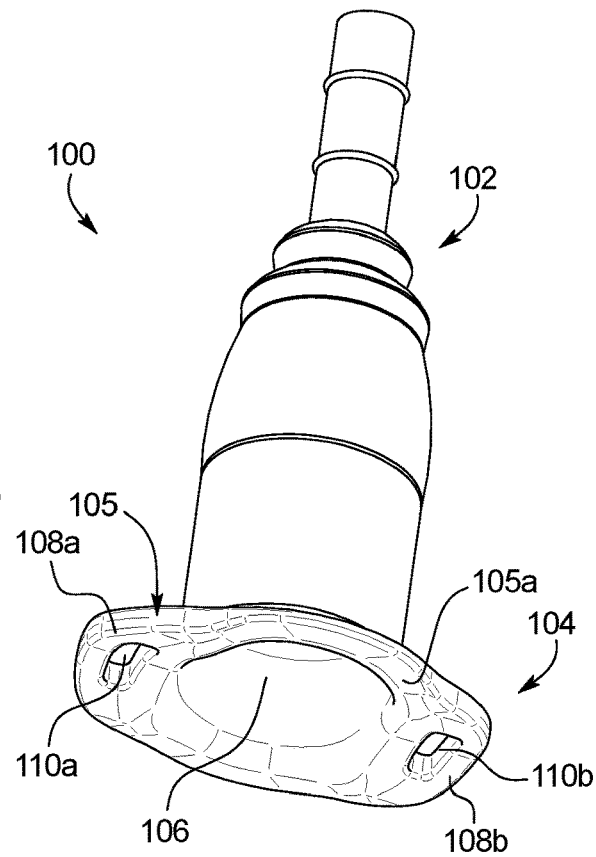
FIG. 2 is a perspective view from below of the male external catheter of FIG. 1.
Figure 3:
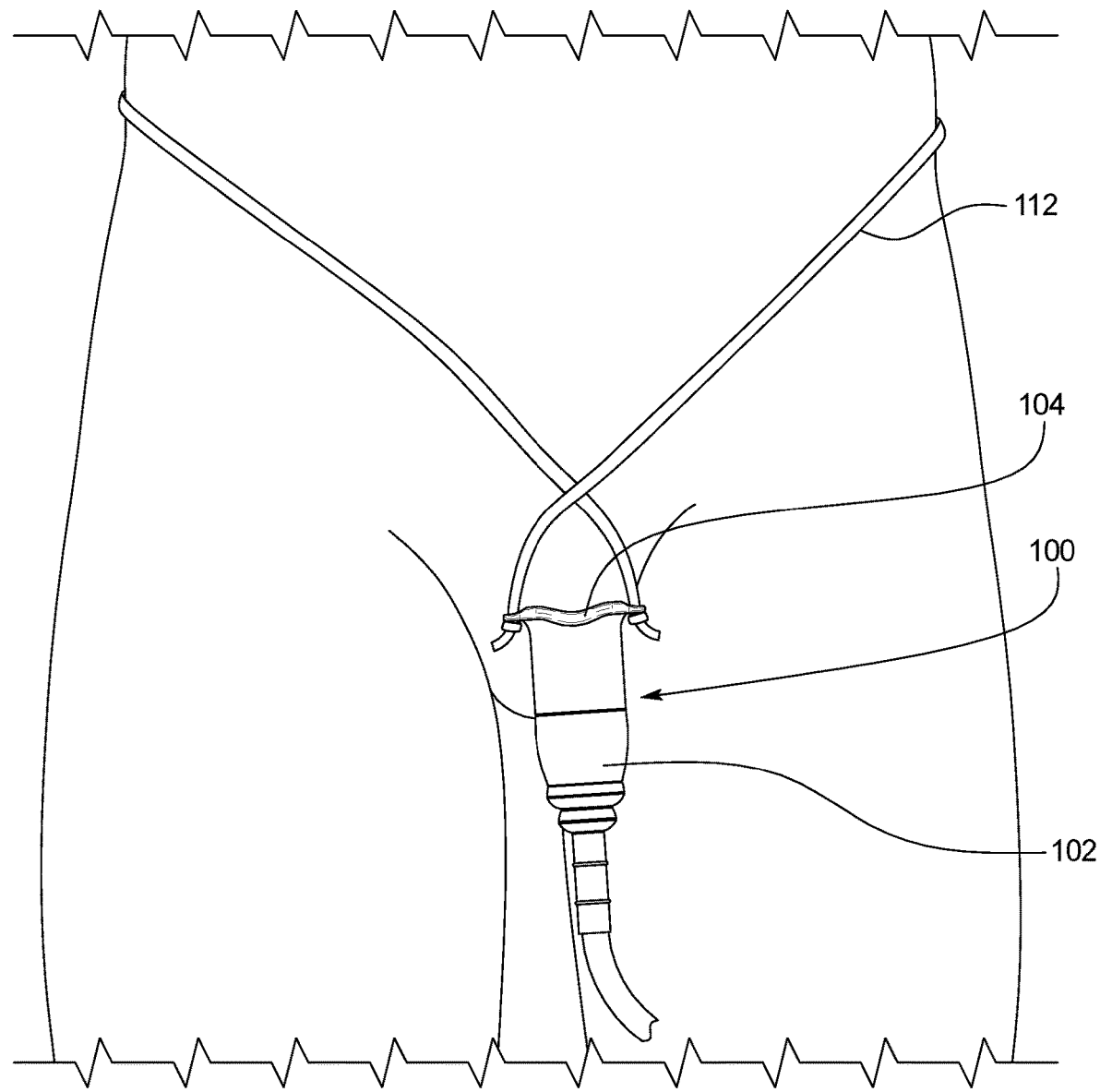
FIG. 3 illustrates the male external catheter of FIG. 1 during use.

FIGS. 1-6B illustrates an example of a male external catheter 100 according to the present disclosure. Referring to FIGS. 1 and 2, the male external catheter or condom catheter 100 includes a body 102 having a tubular shape that extends from a base 104. The base 104 is a planar body 105 providing a frame or structural support for an opening 106 through which the penis extends during use, as shown in FIG. 3. The tubular shape of the body 102 of the male external catheter 100 varies in cross-section along a height H (FIG. 5) thereof.

Figure 4:
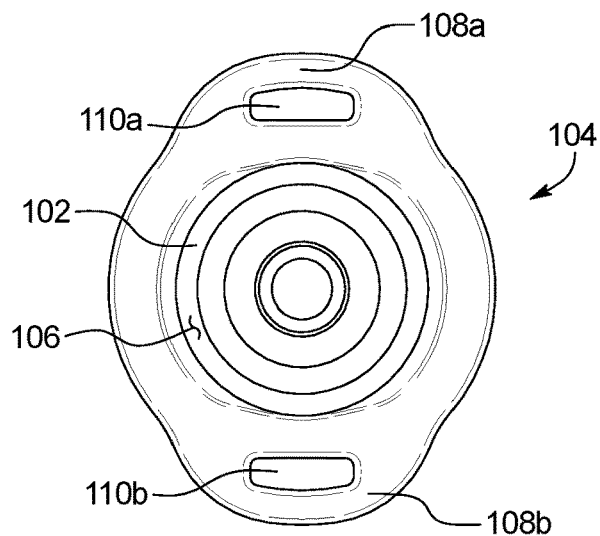
FIG. 4 is a bottom plan view of the male external catheter of FIG. 1.

As shown in FIG. 4, the planar body 105 of the base 104 includes first and second side portions 108a, 108b on opposite sides of the opening 106. Each side portion 108a, 108b has strap opening 110a, 110b for receiving an elastic strap 112. During use, as illustrated in FIG. 3, the elastic strap 112 may be fixedly or removably attached to the strap openings 110a, 110b of the base 104 and extend around the waist of the user to reinforce the positioning of the male external catheter 100 on the patient's body. In some embodiments, the strap openings 110a, 110b have a slot shape.

The opening 106 on the base 104 of the male external catheter 100 defines an expandable sphincter that changes in size so that the opening 106 may conform to a diameter of a penis of the patient. The expandable sphincter provides a near liquid-tight seal between the male external catheter 100 and the penis so that urine may not easily escape. The expandable nature of the sphincter may also provide a comfortable fit for the patient and reduce the incidence of skin irritation as the body 102 of the condom catheter 100 does not slide or substantially shift when positioned on the penis.

Referring to FIGS. 1 and 2, the planar body 105 includes a first planar surface 105a and a second planar surface 105b opposite the first planar surface 105a. In the illustrated embodiment, the first planar surface 105a is contoured to improve comfort and fit during use. The contoured first planar surface 105a is slightly concave. The body 102 of the male external catheter 100 extends from the second planar surface 105b, with the tubular shape thereof formed around the opening 106 of the base 104.

Figure 5:
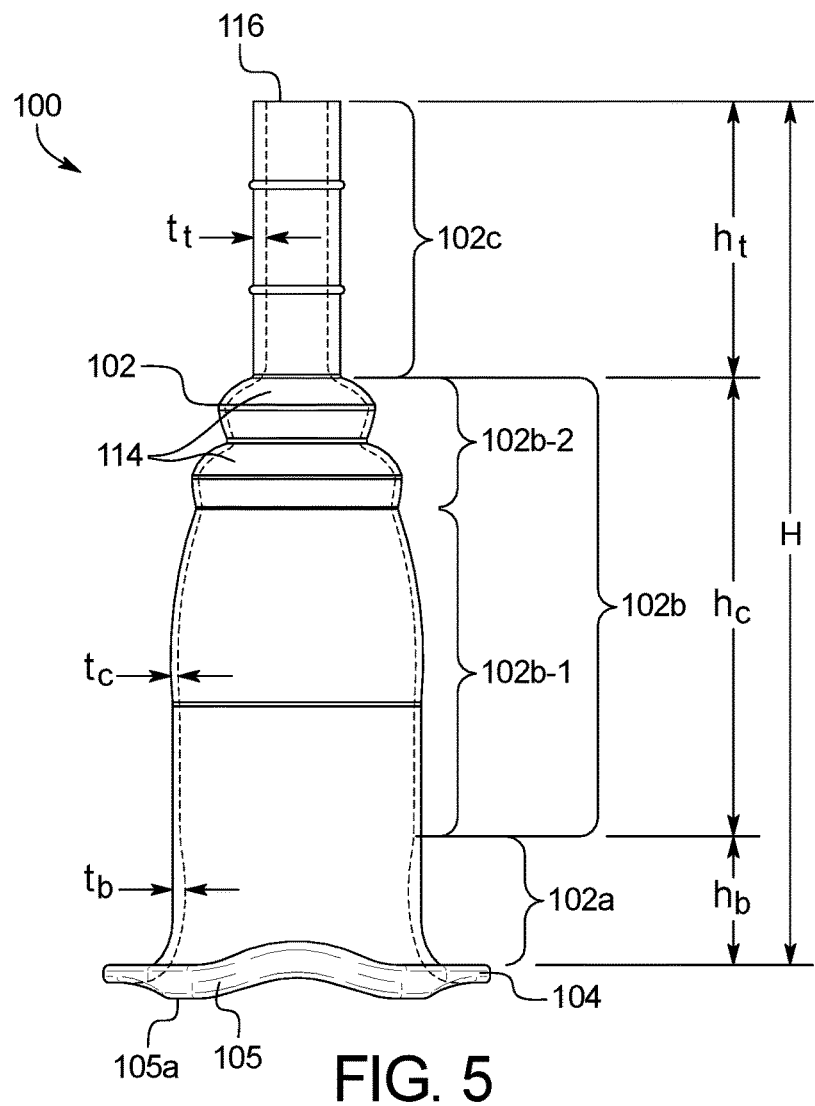
FIG. 5 is a side elevational view of the male external catheter of FIG. 1.

Referring to FIG. 5, the body 102 includes a base portion 102a, a central portion 102b, and a tip portion 102c. The base portion 102a is adjacent to the base 104 and the tip portion 102c is distal from the base 104. The tip portion 102c is configured to connect to tubing of a drainage bag.

Each of the base portion 102a, the central portion 102b, and the tip portion 102c include a base wall thickness $t_b$, a central wall thickness $t_c$, and a tip wall thickness $t_t$, respectively. In the illustrated embodiment, the central wall thickness $t_c$ is less than each of the base wall thickness $t_b$ and the tip wall thickness $t_t$. In some embodiments, the central wall thickness $t_c$ is less than one of the base wall thickness $t_b$ and the tip wall thickness $t_t$. This difference in wall thicknesses enables the central portion 102b of the body 102 to collapse around the user's penis while urine flows through the tip portion 102c and tip into the drainage bag.

In some embodiments, the ratio of the central wall thickness $t_c$ to one or both of the base wall thickness $t_b$ and the tip wall thickness $t_t$ is at least 1:1.1, preferably 1:1.2. In other embodiments, the ratio of the central wall thickness $t_c$ to one or both of the base wall thickness $t_b$ and the tip wall thickness $t_t$ is at least 1:1.5, and in still further embodiments, the ratio of the central wall thickness $t_c$ to one or both of the base wall thickness $t_b$ and the tip wall thickness tris at least 1:2.

The base portion 102a of the body 102 may be formed integrally with the base 104 and has a base height $h_b$ of approximately 0.830 in, although the base height $h_b$ may vary as desired or required during manufacturing. In one embodiment, the base wall thickness $t_b$ is preferably about 0.060 in at the greatest point, although the base wall thickness $t_b$ may vary as desired or as required during manufacturing. In one embodiment, the base wall thickness $t_b$ tapers from a predominant base wall thickness $t_{b-p}$ to the central wall thickness $t_c$ near the juncture of the base portion 102a and the central portion 102b. In one embodiment, the predominant base wall thickness $t_{b-p}$ is about 0.060 in.

The central portion 102b of the body 102 includes a planar section 102b-1 adjacent the base portion 102a and a bellowed section 102b-2 adjacent the tip portion 102c. The bellowed section 102b-2 includes horizontal bellows 114 transverse to the height H of the body 102, and the planar section 102b-1 may include optional vertical ribbing 116 connected to the horizontal bellows 114. The vertical ribs 116 may be evenly positioned along the perimeter of the body 102 near the juncture of the planar section 102b-1 and the bellowed section 102b-2.

In one embodiment, the central portion 102b has a central height $h_c$ of about 1.514 in, although the central height $h_c$ may vary as desired or required during manufacturing. The central wall thickness $t_c$ is preferably about 0.030 in, although the central wall thickness $t_c$ may vary as desired or as required during manufacturing.

The tip portion 102c of the body 102 has a tip height $h_t$ of about 1.315 in, although the tip height $h_t$ may vary as desired or required during manufacturing. The tip wall thickness $t_t$ is preferably about 0.060 in although the tip wall thickness $t_t$ may vary as desired or required during manufacturing. In some embodiments, the tip portion includes horizontal ribbing along the perimeter of the cylindrical body.

Shown in FIG. 5, the height H of the male external catheter 100 extends from the first planar surface 105a of the base 104 to a tip end surface 116.

The male external catheter 100 of the present application may come in different sizes to accommodate differently sized patients. While the dimensions of the structure may vary, the base wall thickness, the central wall thickness, and the tip wall thickness remain the same. In other words, while the diameter of the body may vary between sizes, the central wall thickness is preferably about 0.030 in while the base wall thickness and the tip wall thickness is about 0.060 in.

The male external catheter 100 may come in various sizes. In the embodiment illustrated in FIGS. 1-5, the male external catheter 100 may have the dimensions recited in the following table in reference to FIGS. 6A and 6B for a small-medium size and a medium-large size. It is understood that the dimensions are exemplary only and do not limit the scope of any claims herein, except as may be recited thereby, together with equivalents thereof. The dimensions may vary depending during the manufacturing process or as otherwise desired.

TABLE 1

Figure 6A:
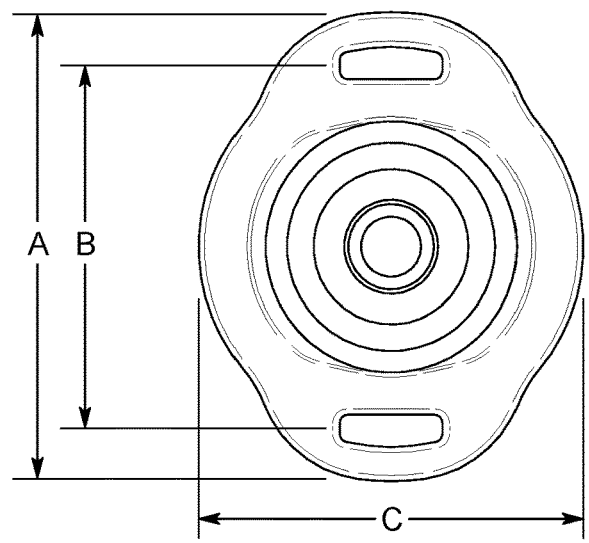
FIGS. 6A and 6B are bottom plan and side elevational views, respectively, of the male external catheter of FIG. 1, illustrating dimensions.
Figure 6B:
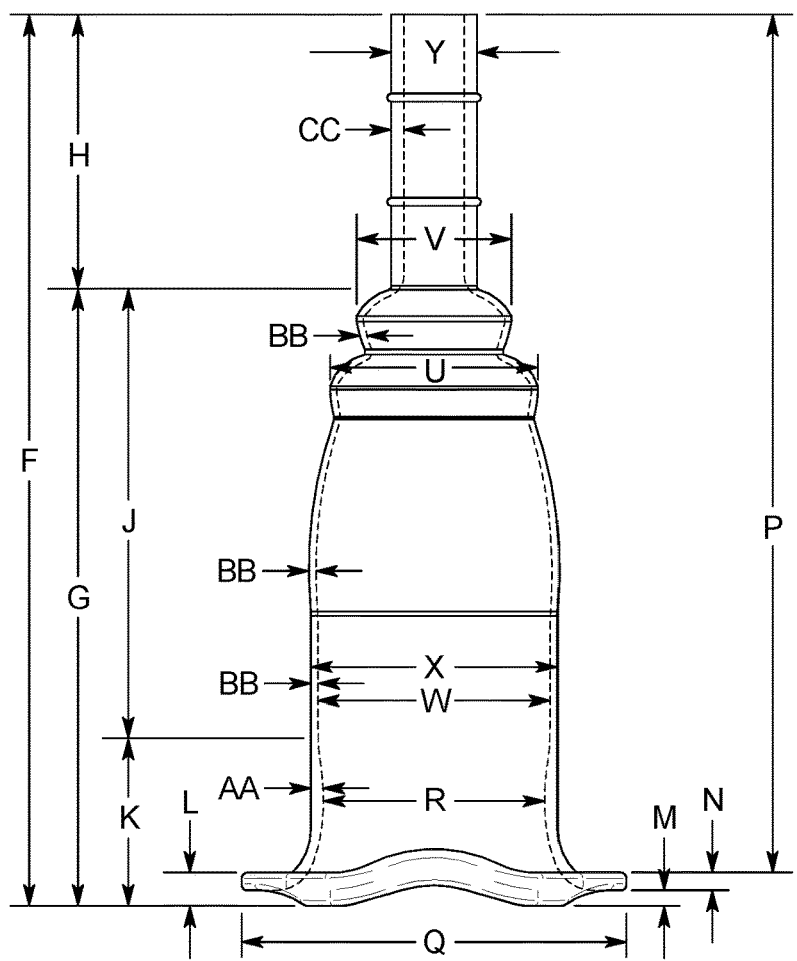

| | Dimensions (in) | |
|---|---|---|
| | Small-Medium Size | Medium-Large Size |
| FIG. 6A | | |
| A | 2.250 | 2.250 |
| B | 1.737 | 1.737 |
| C | 1.842 | 1.842 |
| FIG. 6B | | |
| F | 4.280 | 4.280 |
| G | 2.965 | 2.965 |
| H | 1.315 | 1.315 |
| J | 1.514 | 1.514 |
| K | 0.830 | 0.830 |
| L | 0.260 | 0.160 |
| M | 0.100 | 0.080 |
| N | 0.160 | 0.080 |
| P | 4.280 | 4.280 |
| Q | 1.842 | 1.607 |
| R | 0.827 | 1.062 |
| U | 1.003 | 1.003 |
| V | 0.747 | 0.747 |
| W | 0.887 | 1.122 |
| X | 0.947 | 1.182 |
| Y | 0.410 | 0.410 |
| AA | 0.060 | 0.060 |
| BB | 0.030 | 0.030 |
| CC | 0.060 | 0.060 |

In one embodiment, the male external catheter 100 is made of a silicone rubber compound, although other suitable materials may be used. The silicone rubber compound may be a peroxide-cured silicone elastomer including polydimethylsiloxane with vinyl functional groups. In one embodiment, the compound comprises approximately 70% to approximately 90% by weight polydimethylsiloxane. The silicone rubber material may be hardness (Shore A hardness test) of 20 points, a tensile strength of 800 psi, an elongation at rupture of 800%, and a specific gravity of 1.2. In some embodiments, the male external catheter 100 is latex free. In other embodiments, the body 102 and the base 104 may be composed of the same material or different materials.

During use, the patient is placed in a supine position and the elastic strap is positioned under the lower back of the patient. The opening 106 of the base 104 of the male external catheter 100 is stretched open using index and middle fingers. The height H of the male external catheter 100 is compressed, using thumbs to push the tip portion 102*c* of the body 102 toward the base 104. The penis is then inserted into the stretched, enlarged opening 106, and the base portion 102*a* of the body 102 is pulled and pushed over and above the glans penis towards the base of the penis as far as possible.

A first end of the elastic strap 112 is extended from a first side of the patient across the lower abdomen and secured to the side portion 108 opposite the first side of the patient. A second end of the elastic strap 112 is then extended from a second side of the patient across the lower abdomen and secured to the side portion 108 opposite the second side of the patient. The elastic strap in eff and scope of the present invention and without diminishing its attendant advantages. For example, various embodiments of the systems and methods may be provided based on various combinations of the features and functions from the subject matter provided herein.

What is claimed is:

1. A male external catheter that connects to tubing of a drainage bag, the male external catheter comprising:
  a base having a body and including an opening, wherein the body includes a first surface and a second surface opposite the first surface; and
  a body extending from the second surface and having a tubular shape about the opening of the base, the body including:
    a base portion adjacent to the base and having a base wall thickness;
    a tip portion distal from the base and including a tip configured to connect to the tubing of the drainage bag, wherein the tip portion has a tip wall thickness; and
    a central portion between the base portion and the tip portion and having a central wall thickness;
  wherein the central wall thickness is less than each of the base wall thickness and the tip wall thickness.

2. The male external catheter of claim 1, wherein a ratio of the central wall thickness to one of the base wall thickness and the tip wall thickness is at least 1:1.25.

3. The male external catheter of claim 2, wherein a ratio of the central wall thickness to one of the base wall thickness and the tip wall thickness is at least 1:1.5.

4. The male external catheter of claim 2, wherein a ratio of the central wall thickness to one of the base wall thickness and the tip wall thickness is at least 1:2.

5. The male external catheter of claim 1, wherein the central portion includes a planar section adjacent to the base portion and a bellowed section adjacent to the tip portion.

6. The male external catheter of claim 5, wherein the body has a height extending from the first surface of the base to a tip end surface on the tip, wherein the bellowed section includes horizontal bellows transverse to the height of the body.

7. The male external catheter of claim 1, wherein the base portion has a base height of approximately 0.830 in.

8. The male external catheter of claim 1, wherein the base wall thickness varies along the base height and includes a predominant base wall thickness, and wherein the central wall thickness is less than the predominant base wall thickness.

9. The male external catheter of claim 8, wherein the base wall thickness tapers to the central wall thickness where the base portion of the body meets the central portion of the body.

10. The male external catheter of claim 1, wherein the base and the body comprise a silicone material.

11. The male external catheter of claim 10, wherein the base and body are free from latex.

12. The male external catheter of claim 10, wherein the base and body are free from adhesive.

13. A male external catheter that connects to tubing of a drainage bag, the male external catheter comprising:
  a base having a body with a first surface and a second surface opposite the first surface, wherein the base includes a central opening and first and second strap openings on opposite sides of the central opening; and
  a body extending from the second surface and having a tubular shape about the opening of the base, the body including:
    a base portion adjacent to the base and having a base wall thickness;

a tip portion distal from the base and including a tip configured to connect to the tubing of the drainage bag, wherein the tip portion has a tip wall thickness; and a central portion between the base portion and the tip portion and having a central wall thickness;

wherein the central wall thickness is less than each of the base wall thickness and the tip wall thickness.

14. The male external catheter of claim 13, wherein the first surface of the base has a concave shape.

15. The male external catheter of claim 13, wherein each of the first and second strap openings has a slot shape.

16. A method of using a male external catheter by a user, the method comprising the steps of:

providing the male external catheter comprising:
  a base having a body and including an opening, wherein the body includes a first surface and a second surface opposite the first surface; and
  a body extending from the second surface and having a tubular shape about the opening of the base, the body including:
    a base portion adjacent to the base and having a base wall thickness;
    a tip portion distal from the base and including a tip configured to connect to the tubing of the drainage bag, wherein the tip portion has a tip wall thickness; and
    a central portion between the base portion and the tip portion and having a central wall thickness;
  wherein the central wall thickness is less than each of the base wall thickness and the tip wall thickness;

expanding the opening of the base;

inserting a penis of the user through the opening and into the body; and releasing the opening of the base so that the male external catheter remains in position on the penis without the use of an adhesive.

17. The method of claim 16, further comprising the step of:

causing the central portion of the body of the male external catheter to collapse around the penis by releasing urine into and through the tip portion of the body of the male external catheter.

18. The male external catheter of claim 1, wherein a ratio of the base wall thickness to the central wall thickness to the tip wall thickness is at least 1.25:1:1.25.

19. The male external catheter of claim 1, wherein a ratio of the base wall thickness to the central wall thickness to the tip wall thickness is at least 2:1:2.

20. The male external catheter of claim 1, wherein the central wall thickness is about 0.030 in.

\* \* \* \* \*